US010932862B2

(12) United States Patent
Mechael et al.

(10) Patent No.: US 10,932,862 B2
(45) Date of Patent: Mar. 2, 2021

(54) AUTOMATIC BRAIN PROBE GUIDANCE SYSTEM

(71) Applicant: Alpha Omega Neuro Technologies Ltd., Nazareth (IL)

(72) Inventors: Majid Mechael, Abu Snan (IL); Dan Valsky, Beer-Sheva (IL); Hagai Bergman, Jerusalem (IL); Zvi Israel, Jerusalem (IL)

(73) Assignee: Alpha Omega Neuro Technologies Ltd., Nof HaGalil (IL)

( * ) Notice: Subject to any disclaimer, the term of this patent is extended or adjusted under 35 U.S.C. 154(b) by 361 days.

(21) Appl. No.: 15/572,799

(22) PCT Filed: May 9, 2016

(86) PCT No.: PCT/US2016/031448
§ 371 (c)(1),
(2) Date: Nov. 9, 2017

(87) PCT Pub. No.: WO2016/182997
PCT Pub. Date: Nov. 17, 2016

(65) Prior Publication Data
US 2018/0125585 A1 May 10, 2018

Related U.S. Application Data

(60) Provisional application No. 62/159,336, filed on May 10, 2015.

(51) Int. Cl.
*A61N 1/05* (2006.01)
*A61B 34/20* (2016.01)
(Continued)

(52) U.S. Cl.
CPC .............. *A61B 34/20* (2016.02); *A61B 5/291* (2021.01); *A61B 5/375* (2021.01); *A61N 1/0534* (2013.01); *G06K 9/6297* (2013.01)

(58) Field of Classification Search
CPC ..... A61B 34/20; A61B 5/0478; A61B 5/0482; A61N 1/0534
See application file for complete search history.

(56) References Cited

U.S. PATENT DOCUMENTS 4,603,696 A    8/1986   Cross, Jr. et al.
5,097,835 A    3/1992   Putz
(Continued)

FOREIGN PATENT DOCUMENTS

CN    101516436    8/2009
CN    101829400    9/2010
(Continued)

OTHER PUBLICATIONS

Supplementary European Search Report and the European Search Opinion dated Dec. 6, 2018 From the European Patent Office Re. Application No. 16793310.0. (7 Pages).
(Continued)

*Primary Examiner* — Joseph M Dietrich

(57) ABSTRACT

The disclosure relates to an automatic brain-probe guidance systems. Specifically, the disclosure is directed to a real-time method and system for guiding a probe to the dorsolateral oscillatory region of the subthalamic nucleus in the brain of a subject in need thereof using factored Partially Observable Markov Decision Process (POMDP) via Hidden Markov Model (HMM) represented as a dynamic Bayesian Network (DBN).

30 Claims, 5 Drawing Sheets

(51) Int. Cl.
*A61B 5/291* (2021.01)
*A61B 5/375* (2021.01)
*G06K 9/62* (2006.01)

(56) References Cited

U.S. PATENT DOCUMENTS

| | | |
|---|---|---|
| 5,458,629 A | 10/1995 | Baudino et al. |
| 5,584,873 A | 12/1996 | Shoberg et al. |
| 5,713,922 A | 2/1998 | King |
| 5,833,709 A | 11/1998 | Rise et al. |
| 5,843,148 A | 12/1998 | Gijsbers et al. |
| 6,011,996 A | 1/2000 | Gielen et al. |
| 6,253,109 B1 | 6/2001 | Gielen |
| 6,301,492 B1 | 10/2001 | Zonenshayn |
| 7,033,326 B1 | 4/2006 | Pianca et al. |
| 7,047,084 B2 | 5/2006 | Erickson et al. |
| 7,177,701 B1 | 2/2007 | Pianca |
| 7,668,601 B2 | 2/2010 | Hegland et al. |
| 7,783,359 B2 | 8/2010 | Meadows |
| 7,809,446 B2 | 10/2010 | Meadows |
| 7,877,150 B2 | 1/2011 | Hoegh et al. |
| 7,917,231 B2 | 3/2011 | Farah et al. |
| 7,941,202 B2 | 5/2011 | Hetke et al. |
| 8,000,808 B2 | 8/2011 | Hegland et al. |
| 8,295,944 B2 | 10/2012 | Howard et al. |
| 8,364,272 B2 | 1/2013 | Goetz |
| 8,452,415 B2 | 5/2013 | Goetz et al. |
| 8,473,061 B2 | 6/2013 | Moffitt et al. |
| 8,498,718 B2 | 7/2013 | Meadows |
| 8,532,757 B2 | 9/2013 | Molnar et al. |
| 8,538,513 B2 | 9/2013 | Molnar et al. |
| 8,548,602 B2 | 10/2013 | Moffitt et al. |
| 8,694,127 B2 | 4/2014 | Pianca et al. |
| 8,739,403 B2 | 6/2014 | Hegland et al. |
| 8,755,905 B2 | 6/2014 | Meadows |
| 8,755,906 B2 | 6/2014 | Moffitt et al. |
| 8,788,064 B2 | 7/2014 | Mercanzini et al. |
| 8,792,972 B2 | 7/2014 | Zaidel et al. |
| 8,874,232 B2 | 10/2014 | Chen |
| 8,938,308 B2 | 1/2015 | Meadows |
| 8,977,367 B2 | 3/2015 | Elahi et al. |
| 9,199,090 B2 | 12/2015 | Goetz et al. |
| 2001/0014820 A1 | 8/2001 | Gielen et al. |
| 2003/0212691 A1 | 11/2003 | Kuntala et al. |
| 2005/0065427 A1 | 3/2005 | Magill et al. |
| 2005/0246004 A1 | 11/2005 | Cameron et al. |
| 2006/0265039 A1 | 11/2006 | Bartic et al. |
| 2008/0039709 A1 | 2/2008 | Karmarkar |
| 2008/0082109 A1 | 4/2008 | Moll et al. |
| 2008/0243214 A1 | 10/2008 | Koblish |
| 2008/0243219 A1 | 10/2008 | Malinowski et al. |
| 2009/0054941 A1 | 2/2009 | Eggen et al. |
| 2010/0160771 A1 | 6/2010 | Gielen et al. |
| 2010/0241020 A1* | 9/2010 | Zaidel ............... A61B 5/04001 600/544 |
| 2010/0292602 A1 | 11/2010 | Worrell et al. |
| 2011/0160797 A1 | 6/2011 | Makous et al. |
| 2011/0295350 A1 | 12/2011 | Mercanzini et al. |
| 2011/0301665 A1 | 12/2011 | Mercanzini et al. |
| 2012/0046710 A1 | 2/2012 | DiGiore et al. |
| 2012/0046715 A1 | 2/2012 | Moffitt et al. |
| 2012/0053659 A1 | 3/2012 | Molnar et al. |
| 2012/0101537 A1 | 4/2012 | Peterson et al. |
| 2012/0101552 A1 | 4/2012 | Lazarewicz et al. |
| 2012/0184837 A1 | 7/2012 | Martens et al. |
| 2012/0296230 A1 | 11/2012 | Davis et al. |
| 2013/0066331 A1 | 3/2013 | Chitre et al. |
| 2013/0096642 A1 | 4/2013 | Wingeier |
| 2013/0123600 A1 | 5/2013 | Tscheng |
| 2014/0309714 A1 | 10/2014 | Mercanzini et al. |
| 2015/0031982 A1 | 1/2015 | Piferi et al. |
| 2015/0065839 A1 | 3/2015 | Farah et al. |
| 2015/0066006 A1 | 3/2015 | Srivastava |
| 2015/0265180 A1* | 9/2015 | Venkatesan ............ A61B 5/064 600/378 |
| 2016/0045748 A1 | 2/2016 | Astrom et al. |
| 2019/0069797 A1 | 3/2019 | Naor et al. |
| 2019/0321106 A1 | 10/2019 | Bergman et al. |

FOREIGN PATENT DOCUMENTS

| | | |
|---|---|---|
| CN | 102245253 | 11/2011 |
| CN | 104622468 | 5/2015 |
| EP | 0832667 | 4/1998 |
| EP | 2144665 | 1/2010 |
| JP | 2004-261569 | 9/2004 |
| JP | 2012-531936 | 12/2012 |
| WO | WO 99/36122 | 7/1999 |
| WO | WO 2008/133615 | 11/2008 |
| WO | WO 2011/001322 | 1/2011 |
| WO | WO 2015/173787 | 11/2015 |
| WO | WO 2016/182997 | 11/2016 |
| WO | WO 2017/158604 | 9/2017 |
| WO | WO 2018/0080 | 1/2018 |

OTHER PUBLICATIONS

International Preliminary Report on Patentability dated Jan. 17, 2019 From the International Bureau of WIPO Re. Application No. PCT/IL2017/050763. (8 Pages).

Supplementary European Search Report and the European Search Opinion dated Sep. 23, 2019 From the European Patent Office Re. Application No. 17765991.9. (8 Pages).

International Preliminary Report on Patentability dated Sep. 27, 2018 From the International Bureau of WIPO Re. Application No. PCT/IL2017/050328. (8 Pages).

Corrected International Search Report and the Written Opinion dated Dec. 20, 2016 From the International Searching Authority Re. Application No. PCT/US2016/031448. (9 Pages).

International Preliminary Report on Patentability dated Nov. 23, 2017 From the international Bureau of WIPO Re. Application No. PCT/US2016/031448. (7 Pages).

International Search Report and the Written Opinion dated Nov. 3, 2016 From the International Searching Authority Re. Application No. PCT/US2016/031448. (9 Pages).

International Search Report and the Written Opinion dated Aug. 11, 2017 From the International Searching Authority Re. Application No. PCT/IL2017/050328. (18 Pages).

International Search Report and the Written Opinion dated Nov. 27, 2017 From the International Searching Authority Re. Application No. PCT/IL2017/050763. (15 Pages).

Invitation to Pay Additional Fees dated Jun. 8, 2017 From the International Searching Authority Re. Application No. PCT/IL2017/050328. (2 Pages).

Invitation to Pay Additional Fees dated Sep. 13, 2017 From the International Searching Authority Re. Application No. PCT/IL2017/050763. (2 Pages).

Chaturvedi et al. "Current Steering to Activate Targeted Neural Pathways During Deep Brain Stimulation of the Subthalamic Region", Brain Stimulation, 5(3): 369-377, Jul. 2015.

Chen et al. "Intra-Operative Recordings of Local Field Potentials Can Help Localize the Subthalamic Nucleus in Parkinson's Disease Surgery", Experimental Neurology, 198(1): 214-221, Available Online Jan. 5, 2006.

Chen et al. "Intra-Operative Recordings of Local Field Potentials Can Help Localize the Subthalamic Rucleus in Parkinson's Disease Surgery", Experimental Neurology 198: 214-221, 2006.

Connolly et al. "Spatial Resolution and Heterogeneity of Local Field Potentials in the Globus Pallidus", 6th Annual International IEEE EMBS Conference on Neural Engineering, San Diego, CA, USA, Nov. 6-8, 2013, p. 129-132, Nov. 6, 2013.

Firat Ince et al. "Selection of Optimal Programming Contacts Based on Local Field Potential Recordings From Subthalamic Nucleus in Patients With Parkinson's Disease", Neurosurgery, 67(2): 390-397, Aug. 2010.

Hariz "Deep Brain Stimulation: New Techniques", Parkinsonism and Related Disorders 20(1): 192-196, Jan. 2014.

(56) References Cited

OTHER PUBLICATIONS

Klostermann et al. "Identification of Target Areas for Deep Brain Stimulation in Human Basal Ganglia Substructures Based on Median Nerve Sensory Evoked Potential Criteria", Journal of Neurology, Neurosurgery and Psychiatry, 74(8): 1031-1035, Aug. 2003.
Lempka et al. "Theoretical Analysis of the Local Field Potential in Deep Brain Stimulation Applications", PLOS ONE, 8(3): e59839-1-e59839-12, Mar. 28, 2013.
Litvak et al. "Optimized Beamforming for Simultaneous MEG and Intracranial Local Field Potential Recordings in Deep Brain Stimulation Patients", NeuroImage, 50(4): 1578-1588, Available Online Jan. 4, 2010.
Marmor et al. "Local Vs. Volume Conductance Activity of Field Potentials in the Human Subthalamic Nucleus", Journal of Neurophysiology, 117(6): 2140-2151, Published Online Feb. 15, 2017.
Moran et al. "Real-Time Refinement of Subthalamic Nucleus Targeting Using Bayesian Decision-Making on the Root Mean Square Measure", Movement Disorders, 21(9): 1425-1431, Published Online Jun. 8, 2006.
Rabiner "A Tutorial on Hidden Markov Models and Selected Applications in Speech Recognition", Proceedings of the IEEE, 77(2): 257-286, Feb. 1989.
Telkes et al. "Localization of Subthalamic Nucleus Borders Using Macroelectrode Local Field Potential Recordings",36th Annual International Conference of the IEEE Engineering in Medicine and Biology Society: 2621-2624, Aug. 2014.
Telkes et al. "Localization of Subthalamic Nucleus Borders Using Nacroelectrode Local Field Potential Recordings", 2014 36th Annual International Conference of the IEEE Engineering in Medicine and Biology Society, EMBC, Chicago, IL, USA, Aug. 26-30, 2014, p. 2621-2624, Aug. 26, 2014.
Telkes et al. "Prediction of STN-DBS Electrode Implantation Track in Parkinson's Diseaseby Using Local Field Potentials", Frontiers in Neuroscience, 10(198): 1-16, May 9, 2016.
Trottenberg et al. "Frequency-Dependent Distribution of Local Field Potential Activity Within the Subthalamic Nucleus in Parkinson's Disease", Experimental Neurology, 205(1): 287-291, Available Online Feb. 6, 2007.
Valsky et al. "Stop! Border Ahead: Automatic Detection of Subthalamic Exit During Deep Brain Stimulation Surgery", Movement Disorder, 32(1): 70-79, Published Online Oct. 6, 2016.
Winestone et al. "The Use of Macroelectrodes in Recording Cellular Spiking Activity", Journal of Neuroscience Methods, 266(1): 34-39, Apr. 30, 2012.
Yoshida et al. "Value of Subthalamic Nucleus Local Field Potentials Recordings in Predicting Stimulation Parameters for Deep Brain Stimulation in Parkinson's Disease", Journal of Neurology, Neurosurgery and Psychiatry, 81(8): 885-889, Published Online May 12, 2010.
Zaidel et al. "Delimiting Subterritories of the Human Subthalamic Nucleus by Means of Microelectrode Recordings and a Hidden Markov Model", Movement Disorders, 24(12): 1785-1793, Published Online Jun. 16, 2009.
Zaidel et al. "Subthalamic Span of Beta Oscillations Predicts Deep Brain Stimulation Efficacy for Patients With Parkinson's Disease", Brain, 133(Pt.7): 2007-2021, Advance Access Publication Jun. 9, 2010.
Supplementary European Search Report and the European Search Opinion dated Mar. 10, 2020 From the European Patent Office Re. Application No. 17823773.1. (8 Pages).
Notice of Reasons for Rejection dated Feb. 18, 2020 From the Japan Patent Office Re. Application No. 2017-557984 and Its Translation Into English. (9 Pages).
Notification of Office Action and Search Report dated Mar. 31, 2020 From the State Intellectual Property Office of the People's Republic of China Re. Application No. 201680039601.0. (6 Pages).
Restriction Official Action dated Mar. 27, 2020 from the US Patent and Trademark Office Re. U.S. Appl. No. 16/084,664. (8 pages).
Notification of Office Action and Search Report dated Sep. 21, 2020 From the State Intellectual Property Office of the People's Republic of China Re. Application No. 201780029771.5. (11 Pages).
Translation Dated Apr. 20, 2020 of Notification of Office Action dated Mar. 31, 2020 From the State Intellectual Property Office of the People's Republic of China Re. Application No. 201680039601.0. (2 Pages).
Official Action dated Sep. 11, 2020 from the US Patent and Trademark Office Re. U.S. Appl. No. 16/315,714. (25 pages).
Notice of Reasons for Rejection dated Oct. 6, 2020 From the Japan Patent Office Re. Application No. 2017-557984 and Its Translation Into English. (5 Pages).
Notification of Office Action dated Dec. 1, 2020 From the State Intellectual Property Office of the People's Republic of China Re. Application No. 201680039601.0 and Its Translation Into English. (6 Pages).
Official Action dated Oct. 27, 2020 From the U.S. Patent and Trademark Office Re. U.S. Appl. No. 16/084,664. (31 Pages).
Translation dated Oct. 22, 2020 of Notification of Office Action dated Sep. 21, 2020 From the State Intellectual Property Office of the People's Republic of China Re. Application No. 201780029771.5. (9 Pages).

* cited by examiner

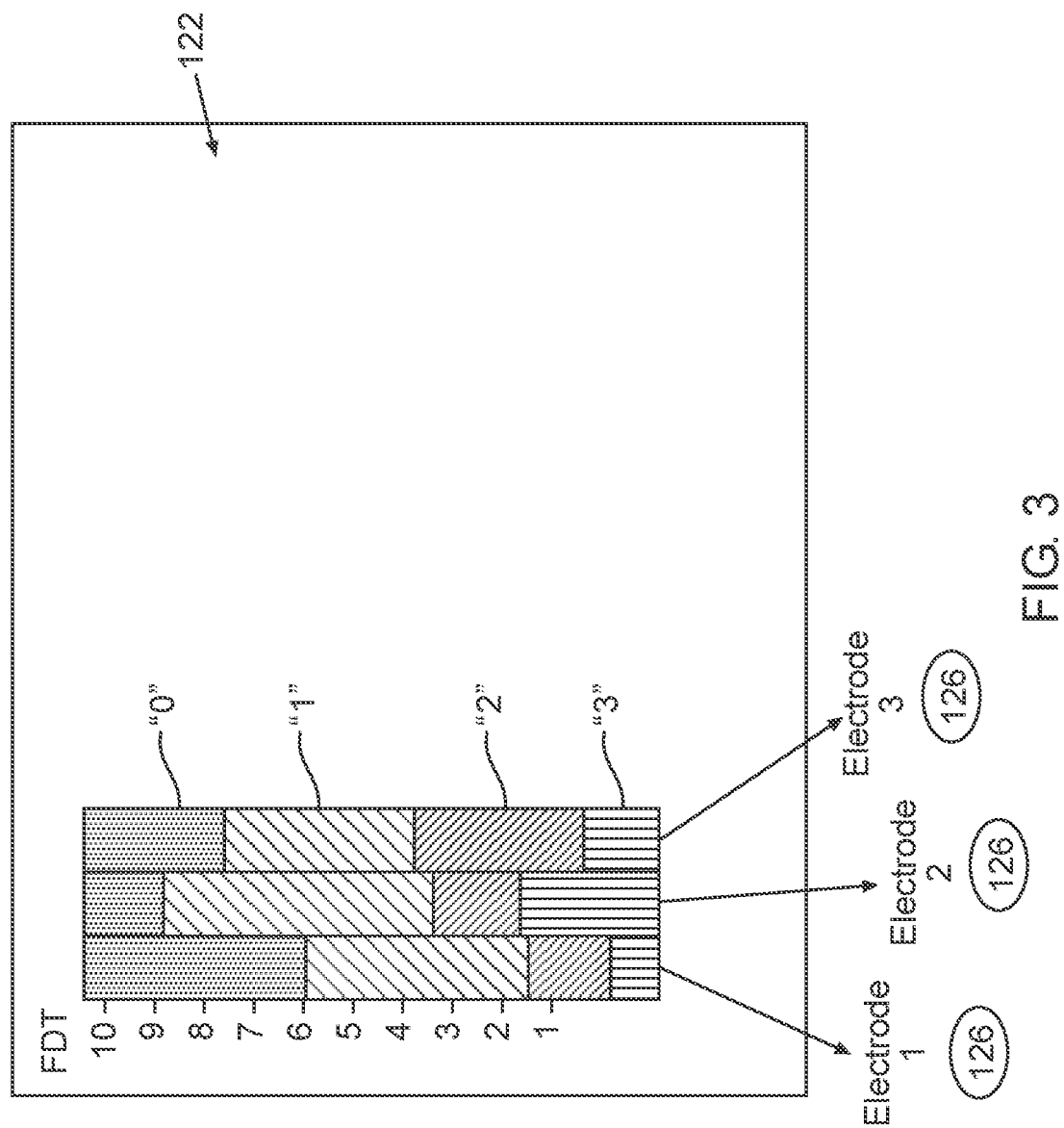

AUTOMATIC BRAIN PROBE GUIDANCE SYSTEM

RELATED APPLICATIONS

This application is a National Phase of PCT Patent Application No. PCT/US2016/031448 having International filing date of May 9, 2016, which claims the benefit of priority under 35 USC § 119(e) of U.S. Provisional Patent Application No. 62/159,336 filed on May 10, 2015. The contents of the above applications are all incorporated by reference as if fully set forth herein in their entirety.

FIELD AND BACKGROUND OF THE INVENTION

The disclosure is directed to an automatic brain-probe guidance systems. Specifically, the disclosure is directed to a real-time method and system for guiding a probe to the dorsolateral oscillatory region of the subthalamic nucleus in the brain of a subject in need thereof using closed stochastic electrophysiological feed back.

Deep brain stimulation (DBS) is a surgical procedure involving the implantation of a medical device called a macroelectrode (also referred to as a "lead", "brain pacemaker", "electrode" or "chronic electrode"), which sends electrical impulses to specific parts of the brain. DBS in select brain regions has provided noticeable therapeutic benefits for otherwise treatment-resistant movement and affective disorders such as chronic pain, Parkinson's disease, tremor, dystonia and depression. At present, the procedure is used only for patients whose symptoms cannot be adequately controlled with medications. DBS directly changes brain activity in a controlled manner, and its effects are reversible (unlike those of lesioning techniques). DBS uses the surgically implanted, battery-operated medical neurostimulator to deliver electrical stimulation to targeted areas in the brain that control movement, blocking the abnormal nerve signals that cause tremor and PD symptoms.

Before the procedure, a neurosurgeon uses magnetic resonance imaging (MRI) or computed tomography (CT) scanning to identify and locate the exact target within the brain. For treating movement disorders, these targets are areas that control 5 movement, such as the thalamus, subthalamic nucleus, and globus pallidus where electrical nerve signals generate the undesired symptoms.

DBS systems typically consist of three components: the macroelectrode, the extension, and the neurostimulator. The macroelectrode—a thin, insulated wire—is inserted through a small opening in the skull and implanted in the brain. The tip of the electrode is positioned within the targeted brain area.

The extension is an insulated wire that can then be passed under the skin of the head, neck, and shoulder, connecting the lead to the neurostimulator. The neurostimulator (the "battery pack") is the third component and is usually implanted under the skin near the collarbone. In some cases it may be implanted lower in the chest or under the skin over the abdomen.

Once the system is in place, electrical impulses are sent from the neurostimulator up along the extension wire and the lead and into the brain. These impulses interfere with and block the electrical signals that cause the undesired symptoms. The person has the possibility to turn the DBS off if required.

Accordingly, accurate and fast guidance of the macroelectrode, which is critical in order to improve the effectiveness of the installed macroelectrode. Thus, there is a need in the field to accurately pilot the macroelectrode to the target region in the most precise manner available.

SUMMARY OF THE INVENTION

Provided herein are embodiments of automatic brain-probe guidance systems.

In an embodiment, provided herein is a method of automatically guiding a driver coupled brain probe to a region of interest in the brain of a subject in need thereof, comprising: based on a predetermined insertion trajectory, positioning the brain probe toward the region of interest, the brain probe having a proximal end and a distal end coupled to a driver; using a predetermined step size, translating the brain probe toward the region of interest; recording a neurophysiological response by the brain probe along the predetermined insertion trajectory; based on the recorded neurophysiological response by the brain probe, calculating a plurality of predetermined observation elements; constructing a Bayesian Network for each observation element; combining the plurality of Bayesian Networks constructed for each observation element thereby creating a Dynamic Bayesian Network including the plurality of the predetermined observation elements; based on the Dynamic Bayesian Network, constructing a Factored Partially Observable Markov Decision Process, wherein the Partially Observable Markov Decision Process (POMDP) further comprises relations between the predetermined observation elements; based on the POMDP, determining a distance step to advance the brain probe along the insertion trajectory; using the driver, automatically advancing the brain probe toward the region of interest along the insertion trajectory; and repeating the step of determining the distance step and advancing the brain probe to the location of interest.

In yet another embodiment, provided herein is an automatic brain-probe guidance system comprising: a brain probe having a proximal end and a distal end, the proximal end configured to record a neurophysiological response, and the distal end operably coupled to a driver; the driver, operably coupled to the brain probe; a processing module in communication with the brain probe and the driver; a controller operably coupled to the driver; and a display, in communication with the processing module.

BRIEF DESCRIPTION OF THE SEVERAL VIEWS OF THE DRAWINGS

The features of the automatic brain-probe guidance systems and methods relating thereto described herein, will become apparent from the following detailed description when read in conjunction with the drawings, which are exemplary, not limiting, and wherein like elements are numbered alike in several figures and in which:

FIG. 3 illustrates a simplified pictorial of the graphic user interface shown on a display while using an embodiment of the automatic brain-probe guidance systems.

Figure 1:
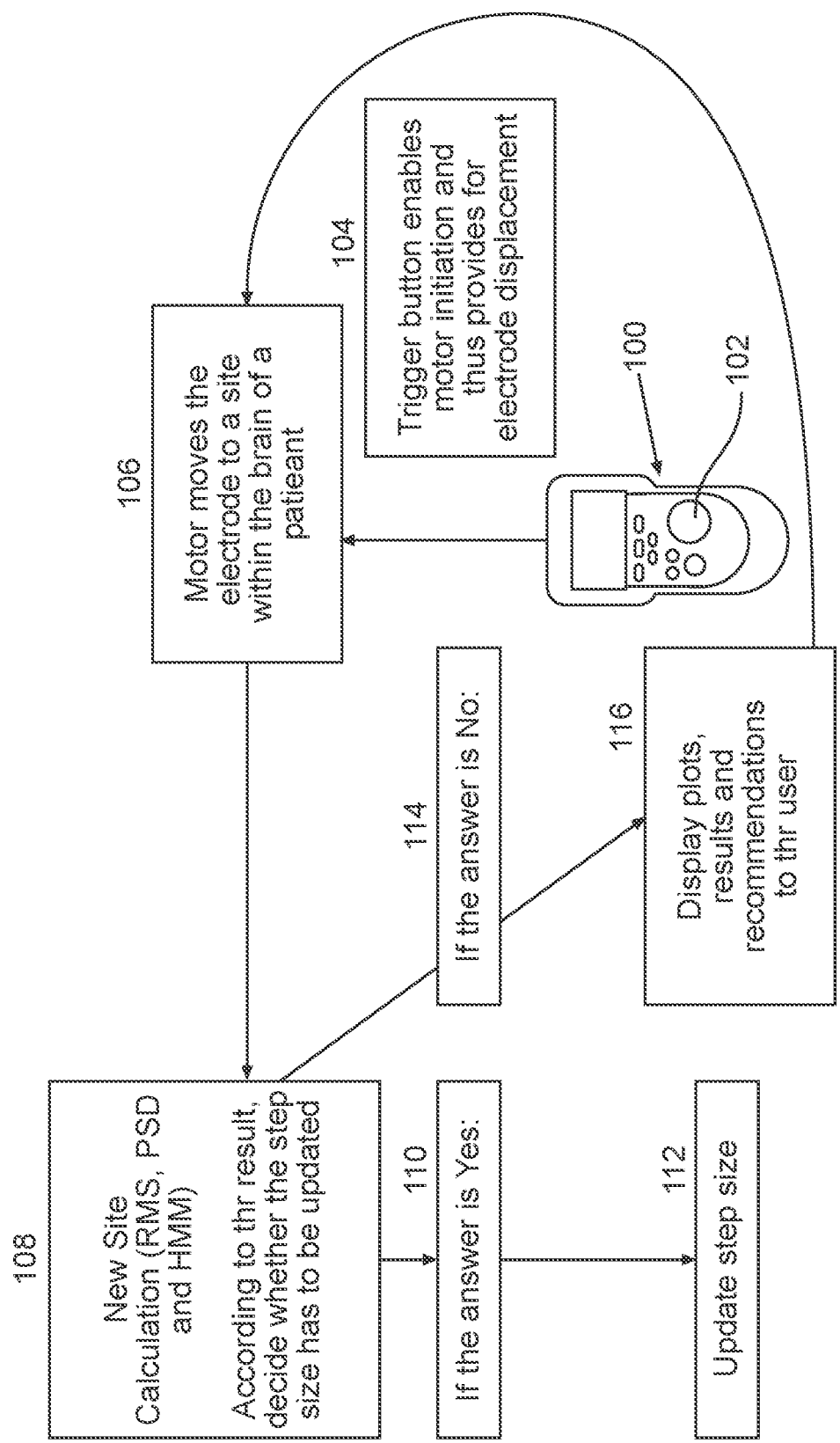
FIG. 1, is a simplified block diagram illustrating the use of an embodiment of the automatic brain-probe guidance systems.

While the disclosure is amenable to various modifications and alternative forms, specifics thereof have been shown by way of example in the drawings and will be further described in detail hereinbelow. It should be understood, however, that the intention is not to limit the disclosure to the particular embodiments described. On the contrary, the intention is to cover all modifications, equivalents, and alternatives.

DESCRIPTION OF SPECIFIC EMBODIMENTS OF THE INVENTION

The disclosure relates in one embodiment to automatic brain-probe guidance systems.

The disclosure provides for an automatic guidance system for piloting a probe (e.g. MER) to a target region in the brain in order to treat a Parkinson Disease. Surgical treatment for advanced Parkinson's disease (PD) includes deep brain stimulation (DBS) of the subthalamic nucleus (STN), which has proven to be safe and beneficial over time. During surgery for implanting an STN DBS macroelectrode, microelectrode recording (MER) is often utilized to verify localization of the STN physiologically. To implant the macroelectrode successfully within the optimal location (probably the sensoridriver portion of the STN), accurate demarcation of the patient's STN (based on the MERs) is required. This includes derivation of the entry and exit points of the STN across the MER trajectory, as well as localization of the sensoridriver area within the STN.

The STN can be divided into three (sensoridriver, limbic, and cognitive/associative) functional territories, each broadly involved in its respective basal ganglia-thalamocortical loop. The sensoridriver region of the STN is primarily located dorsolaterally, the same location that seems to provide optimal therapeutic benefit to patients undergoing STN DBS. Furthermore, it has been shown that local field potential and single unit (when averaged across patients) beta oscillatory activity is generated largely within the dorsolateral portion of the STN. This was also established according to the description of Applicant's prior U.S. Pat. No. 8,792,972 (incorporated herein by reference in its entirety) demonstrating there is correspondence between the dorsolateral oscillatory region (DLOR) and the sensoridriver region of the STN, and that beta-oscillatory activity could possibly predict the most effective contact for STN DBS.

In an embodiment, provided herein is an automated guidance system for piloting a brain probe (e.g., MER) to a region of interest in the brain by identifying subterritories within the STN and thus aiding the neurosurgeon in implanting the DBS macroelectrode in the optimal location or simply be used to estimate the transitions of a MER trajectory. Additionally provided is a real-time method for guiding a probe, such as MER within the brain and delimit the outer boundaries of the STN as well as an intra-STN (DLOR-ventral) boundary during surgery based on the beta range root mean square (RMS) and power spectral density (PSD) of the oscillatory neuronal activity recorded by the MERs, using a Hidden Markov Model (HMM) and Markov decision making models.

The HMM or factorial HMM can be used, for example, offline to automatically detect the trajectory state transitions, or semi-online at the end of a trajectory during STN DBS surgery to help refine demarcation of the sensoridriver STN for macroelectrode implantation. Localization of the DLOR-ventral transition can aid the neurosurgeon in deciding which MER track to implant, when multiple electrodes are used for MER, and in implanting the macroelectrode at the optimal depth.

Accordingly and in an embodiment, provided herein is a method of automatically guiding a driver coupled brain probe to a region of interest in the brain of a subject in need thereof, comprising: based on a predetermined insertion trajectory, positioning the brain probe toward the region of interest, the brain probe having a proximal end and a distal end coupled to a driver; using a predetermined step size, translating the brain probe toward the region of interest; recording a neurophysiological response by the brain probe along the predetermined insertion trajectory; based on the recorded neurophysiological response by the brain probe, calculating a plurality of predetermined observation elements; constructing a Bayesian Network for each observation element; combining the plurality of Bayesian Networks constructed for each observation element thereby creating a Dynamic Bayesian Network including the plurality of the predetermined observation elements; based on the Dynamic Bayesian Network, constructing a Factored Partially Observable Markov Decision Process, wherein the Partially Observable Markov Decision Process (POMDP) further comprises relations between the predetermined observation elements; based on the POMDP, determining a distance step to advance the brain probe along the insertion trajectory; using the driver, automatically advancing the brain probe toward the region of interest along the insertion trajectory; and repeating the step of determining the distance step and advancing the brain probe to the location of interest.

The number of steps to be taken and the size of each step can be determined by the signal processing module. In certain embodiments, the size of each step becomes smaller as the electrode approaches the estimated target region.

The disclosure provides a real-time method and system for guiding a probe to, for example, the dorsolateral oscillatory region of the subthalamic nucleus in the brain of a subject in need thereof using closed stochastic electrophysiological feedback loop optimization.

As used herein the term "stochastic electrophysiological feed back loop" refer to operation with an adequately formulated objective function (for example, the expert determined reference for the location of the estimated location of a dorsolateral oscillatory region (DLOR) of the STN along the selected insertion trajectory), which compares a current observation element value, with a predetermined and/or desired target value and then calculates the difference or the "fit" between the two. The return-value of this objective function drives the evolutionary optimization process that generates the list of steps (responsible for insertion depth along the trajectory) of translational and/or rotational movements of the brain probe coupled to the driver and display.

It is also appreciated that many kinds of probes may be used in connection with the systems and methods described herein. For example, EEG electrodes can be used, however it will be appreciated that any kind of medical electrodes comprising conducting and recording contacts, for obtaining various physiological (neurological and others) characteristics of a subject's brain may be used. These can be, for example, EMG, EKG, ERP, EP, VEP, SSEP medical electrodes or a combination comprising one or more of the foregoing electrodes. Other sensors may be similarly inserted, and used in conjunction with the systems and methods described herein, and can be for example; temperature sensors, (NIR e.g.,) oxygen sensors, current sensors, and the like. Accordingly, the systems for automatic brain-probe guidance described herein can further comprise a sensor array configured to provide additional information useful for surgical operation. The number and/or types of electrodes to be inserted remains to the discretion of the medical team in charge of the procedure. Adding more electrodes increases the chances a trajectory to go through the optimal target location, while at the same time also increases the chances causing damage along the trajectory, for example, going through a small blood vessel. Typically, the medical team chooses one to five electrodes to be inserted The region of interest for which the brain probe guidance systems and methods described herein are guided to, can be a sub-territory of the subthalamic nucleus (STN), for example, dorsolateral oscillatory region (DLOR) of the STN.

STN target coordinates can be determined as a composite of indirect anterior commissure-posterior commissure atlas based location and/or using direct T2 magnetic resonance imaging (MRI), with the final STN position being verified using, for example, postoperative computerized tomography (CT) fused with the preoperative MRI and displayed using the display systems described and claimed.

The neurophysiological response elements, or activity described herein, can be acquired via, for example, polyimide coated tungsten microelectrodes. For both the left and right hemispheres, a single trajectory can be selected, starting, for example, at 10 mm above the calculated target (e.g., center of the lateral STN, or the dorsolateral oscillatory region (DLOR) of the STN). Using a driver coupled to the MER, the electrodes (or brain probe) can be configured to be advanced in small discrete steps, toward the estimated region of interest (ROI). Step size can range, for example, from between about 50 µm and about 500 µm and be controlled to achieve optimal unit recording and identification of upper and lower borders of the STN. For example, shorter steps (e.g., ~100 µm) can be used when the electrode was advanced closer to the goal location of the STN. The systems and methods described, can be configured to provide, for example, a 2-second signal stabilization period after electrode movement cessation, with responses recorded for a minimum of, for example 5 seconds.

In an embodiment, the neurophysiological response recorded by the brain probe used in the methods and systems for automatically guiding a brain probe to a region of interest described herein, can be neuronal firing rate, local field potential or a combination of neurophysiological responses comprising one or more of the foregoing, for example, by recording discharges from the advancing probe (or electrode) and analyzing the recording of the discharges within the beta frequency band range to determine an area of beta oscillatory activity. Beta (about 15-30 Hz) oscillatory activity in the subthalamic nucleus (STN) has been reported to greatly increase in Parkinson's Disease (PD) patients and may interfere with movement execution (Cassidy et al., 2002; Levy et al., 2002; Kuhn et al., 2004; 2005; Williams et al., 2003; 2005). Dopaminergic medications decrease beta activity (Levy et al., 2002) and deep brain stimulation (DBS) in the STN may alleviate PD symptoms by disrupting this oscillatory activity. Depth recordings in PD patients have demonstrated beta oscillatory local field potential (LFP) activity in STN (Levy et al., 2002; Kuhn et al., 2005). Beta oscillatory LFP activity in the STN has been shown to be coherent with cortical EEG and contralateral EMG (Williams et al., 2002; Marsden et al., 2001).

Accordingly, the plurality of observation elements based on the recorded neurophysiological response used in the methods and systems for automatically guiding a brain probe to a region of interest described herein, can be power spectral density (PSD) and/or root mean square (RMS) of the beta oscillatory activity values.

For the power spectral density (PSD) calculations, the raw signal can be rectified by the "absolute" operator and the mean subtracted, to expose the frequency band of interest (e.g, below about 70 Hz, for example, between about 15 Hz and about 30 Hz). The average PSD can be calculated in each location along the trajectory using, for example, Welch's method with about a 1 second Hamming window (with predetermined percentage overlap, e.g., 10%) and zero padding, resulting in a spectral resolution of ⅓ Hz. For each recording (or observation), the PSD can be normalized by the total power of the signal between 2-200 Hz. A plot of the PSD as a function of estimated distance to target (EDT) for the predetermined trajectory can constructed and displayed using the display means provided. In addition, PSD can be used as a marker for the DLOR of the STN based on the increased beta oscillatory activity.

Likewise, entry and exit from the STN can be marked primarily by a dramatic increase and decrease in normalized RMS (NRMS). The NRMS and PSD of an example trajectory, as a function of estimated distance to target (EDT), can therefore be used to guide the advance of the brain probe along the selected trajectory.

The number of the minimal Root Mean Square (RMS) values may be selected and normalized, for example five minimal RMS values may be utilized. Alternatively, a particular number of the first measured RMS values maybe utilized for normalization purposes. Normalization based on minimal RMS values can substantially facilitate noise reduction. At a minimum, the synthesized Dynamic Bayesian Network or HMM can be configured to distinguish between two regions (inferred states) inside the target region or outside the target region. In many cases, the Dynamic Bayesian Network can be trained to distinguish between more than two inferred regions (states).

Training the Dynamic Bayesian Network or HMM can involve entering a statistically significant number of trajectory data reference cases comprising for each point along the insertion trajectory power spectral analysis values, where a human expert assigns to each point in the insertion trajectory, the correct region it is in. The Dynamic Bayesian Network can then study the statistical relations in the data of the reference cases, so that given a new case (trajectory) with only power spectral analysis values (e.g., mean and max Beta PSD) for points along the insertion trajectory, the Dynamic Bayesian Network can build a trajectory model assigning to each point (observation value) along the insertion trajectory the (hidden) state with the highest probability. Assigning the (hidden) state can take into account not only the power spectral analysis values recorded at the incremental stochastic step, but also the power spectral analysis values of part or all the points along the insertion trajectory.

Moreover, the Dynamic Bayesian Network trajectory model serves in an embodiment, as a statistical reference based for analyzing new insertion trajectories and assigning the highest probability state to each location along the insertion trajectory.

In order to estimate the state (e.g., the DLOR of the STN, the region of the insertion trajectory immediately before the STN, the region inside the nonoscillatory STN, or the region of the STN immediately following the STN), and whether the electrode is in one of the of the electrode at each step (depth) across the trajectory based, for example, on the recorded and analyzed observation elements (e.g., NRMS and PSD), a Hidden Markov Model (HMM), or, in another embodiment, factored HMM can be used.

A typical trajectory state sequence could go through all four states consecutively. However, since not all trajectories produce recordable oscillatory observations in the presumed DLOR of the STN, a trajectory could skip that state. In addition, a trajectory could terminate end in in the nonoscillatory STN (a MER trajectory that was terminated before exiting the STN).

The step of positioning the brain probe toward the region of interest used in the methods and systems for automatically guiding a brain probe to a region of interest described herein, can be preceded by providing reference values for each of the plurality of observation elements for a statistically-significant number of locations along the insertion trajectories. In other words, the methods provided can further comprise an initial step of training the (e.g., factorial) HMM by providing reference data of a statistically-significant number of insertion trajectories, whereby states along each insertion trajectory are assigned observation elements' values (e.g., mean beta PSD, max beta PSD and NRMS of the beta oscillatory activity) by an expert to one of the states disclosed herein, as well as the observation elements associated with at least another region, for example, the region in the insertion trajectory within the substantia nigra (SNR).

Identification of the transition to SNR area can be advantageous, because this area in the brain also exhibits significant neurophysiological signals (or emissions) that may be used as target for neurostimulation in the treatment of, for example, Parkinson's disease (PD).

The methods describe, which can be implemented in the systems provided, can further comprise assigning to each location (or hidden state) along the insertion trajectory a probability value illustrating the probability of each observation element per HMM state. The maximum likelihood estimate of the HMM state-transition and emission (the observation value) probability matrices can be estimated based, for example, on known (in other words, human expert defined) state sequences. The inferred HMM state sequence can be calculated as the most probable sequence beginning with the HMM in state 1 (before the STN) before the first observation (using for example, Viterbi algorithm).

The methods and systems for automatically guiding a brain probe to a region of interest described herein, can further comprise removing the inserted probe and inserting a macroelectrode into the region of interest, e.g., the DLOR of the STN, and proceeding to produce deep brain simulation (DBS) for treatment of a neurodegenerative disease and/or disorder, for example, a brain injury, a neurodegenerative disorder, stroke, epilepsy, or Parkinson's disease.

The methods for automatically guiding a brain probe to a region of interest described herein, can be implemented in the systems described herein. Accordingly, provided herein is an automatic brain-probe guidance system (or any collection of systems or sub-systems that individually or jointly execute a set, or multiple sets, of instructions to perform one or more steps of the methods described herein) comprising: a brain probe having a proximal end and a distal end, the proximal end configured to record a neurophysiological response, and the distal end operably coupled to a driver; the driver, operably coupled to the brain probe; a signal processing module in communication with the brain probe and the driver; a controller operably coupled to the driver; and a display, in communication with the signal processing module.

The term "coupled", including its various forms such as "operably coupled", "coupling" or "coupleable", refers to and comprises any direct or indirect, structural coupling, connection or attachment, or adaptation or capability for such a direct or indirect structural or operational coupling, connection or attachment, including integrally formed components and components which are coupled via or through another component or by the forming process (e.g., an electromagnetic field). Indirect coupling may involve coupling through an intermediary member or adhesive, or abutting and otherwise resting against, whether frictionally (e.g., against a housing) or by separate means without any physical connection.

The term "signal processor" as used herein refers in an embodiment, to a power source, a pre-amplifier, an amplifier, an A/D and/or D/A converter, or a module or system comprising one or more of the foregoing.

Likewise, the term "module" is understood to encompass a tangible entity, be that an entity that is physically constructed, specifically configured (e.g., hardwired), or temporarily (e.g., transitorily) configured (e.g., programmed) to operate in a specified manner or to perform part or all of any operation described herein. Considering examples in which modules are temporarily configured, each of the modules need not be instantiated at any one moment in time. For example, where the modules comprise a general-purpose hardware processor configured using software, the general-purpose hardware processor may be configured as respective different modules at different times. Software may accordingly configure a hardware processor, for example, to constitute a particular module at one instance of time and to constitute a different module at a different instance of time.

Further, term "communicate" (and its derivatives e.g., a first component "communicates with" or "is in communication with" a second component) and grammatical variations thereof are used to indicate a structural, functional, mechanical, electrical, or optical relationship, or any combination thereof, between two or more components or elements. As such, the fact that one component is said to communicate with a second component is not intended to exclude the possibility that additional components can be present between, and/or operatively associated or engaged with, the first and second components. Furthermore, the term "electronic communication" means that one or more components of the multi-mode optoelectronic observation and sighting system with cross-platform integration capability described herein are in wired or wireless communication or internet communication so that electronic signals and information can be exchanged between the components.

The signal processing module used in the guidance systems described herein can further comprise a neurophysiological response processor in communication with the brain probe, the processor comprising a memory having a processor-readable media thereon with a set of executable instructions thereon configured to: record a plurality of neurophysiological responses; and based on the recorded neurophysiological response by the brain probe, calculate a plurality of predetermined observation elements.

The signal processing module can also comprise a step determining processor, in communication with the driver and neurophysiological response processor, the step determining processor comprising a memory having a processor-readable media thereon with a set of executable instructions configured to: construct a Bayesian Network for each observation element; combine the plurality of Bayesian Networks constructed for each observation element thereby creating a Dynamic Bayesian Network including the plurality of the predetermined observation elements; based on the Dynamic Bayesian Network, construct a Factored Partially Observable Markov Decision Process, wherein the Partially Observable Markov Decision Process (POMDP) further comprises relations between the predetermined observation elements; and based on the POMDP, determine a distance step to advance the brain probe along the insertion trajectory.

While the processor-readable medium can be a single medium, the term "processor-readable media" includes a single medium or multiple media, such as a centralized or distributed database, and/or associated caches and servers that store one or more sets of executable and other instructions. The term "processor-readable medium" may also include any medium that is capable of storing, encoding or carrying a set of instructions for execution by a processor or that cause a computer system or processor to perform any one or more of the methods or operations disclosed herein.

For example, the processor-readable medium can include a solid-state memory such as a memory card or other package that houses one or more non-volatile read-only memories. Further, the processor-readable medium can be a random access memory or other volatile re-writable memory. Additionally, the processor-readable medium can include a magneto-optical or optical medium, such as a disk or tapes or other storage device to capture neurophysiological response such as, for example, mean beta power spectral density (PSD) and/or maximum beta PSD and/or root mean square (RMS) of the beta oscillatory activity values, neuronal firing rate, local field potential or a combination of neurophysiological responses comprising one or more of the foregoing.

A digital file attachment to an e-mail or other self-contained information archive or set of archives may be considered a distribution medium that is equivalent to a tangible storage medium. Accordingly, the disclosure is considered to include any one or more of a processor-readable medium or a distribution medium and other equivalents and successor media, in which data or instructions may be stored.

In an embodiment, the set of executable instructions in the neurophysiological response processor can be further configured to: analyze the neurophysiological response within the beta frequency band range (e.g., between about 15 Hz to about 30 Hz) to determine a value of beta oscillatory activity (in other words, an observed value), wherein the plurality of observation element based on the recorded neurophysiological response is a mean beta power spectral density (PSD) and/or maximum beta PSD and/or root mean square (RMS) of the beta oscillatory activity values. Each of which or a combination thereof, which can be used with the Dynamic Bayesian Network synthesized, to infer the hidden state at which the electrode is positioned and determine estimated distance to the target region of interest (ETD).

Moreover, the set of executable instructions in the step-determining-processor used in the guidance systems described, as a part of the signal processing module, can further be configured to assign to each of a plurality of locations (or hidden/partially observable states) along the insertion trajectory—a probability value. The locations or in other words, inferred/hidden or partially observable states can be the DLOR of the STN and/or the region of the insertion trajectory immediately before the STN and/or the region inside the nonoscillatory STN and/or the region of the STN immediately following the STN.

The memory in the step-determining-processor (which in an embodiment, can be the same as the step-determining-processor) can further have stored thereon known reference (or inferred) values (or observed nodes for representation of HMM as DBN) for each of the plurality of observation elements for the locations (or hidden states) along the insertion trajectory, as well as, in an embodiment, for each of the plurality of observation elements for the region inside the substantia nigra (SNR).

The brain probe used in the guidance systems described herein can be, for example, a stimulating and or recording electrode. Moreover, the guidance system can further comprise a macroelectrode, configured to provide deep brain stimulation. Stimulating electrophysiological response and/or recording electrophysiological evoked response in the systems and methods described herein can comprise stimulating, recording or both stimulating and recording signals differentially, single ended or both differentially and single ended. For example, a differential sensing configuration can include a tip electrode used as the sensing electrode and a ring electrode used as a reference electrode. Typical tip-to-ring spacing can be approximately 10 mm but may be greater or less than 10 mm. Other differential sensing configurations using any type of available electrodes can be used. During differential sensing, both the sensing electrode and the reference electrode can be positioned along a mapped site, such as within a brain region or along a nerve branch, such that both electrodes are subjected to change in electrical potential caused by an electrophysiological event in the brain, for example, that resulting from transitioning between various states along the insertion trajectory.

Likewise, single ended sensing electrode configurations can comprise a sensing electrode in contact with a region of interest, paired with a reference electrode placed away from the region of interest and is sought to be advanced to the region of interest, such that the reference electrode is not initially subjected to changes in electrical potential caused by electrophysiological events occurring at the site.

Recording the observation elements described herein can be configured to be performed between two adjacent macro-contacts, for example a tip contact and a ring macro contact spaced between about 20 μm and about 500 μm from the tip contact (or electrode) by, for example, recording differential local field potential (LFP) between the two contacts, wherein one contact is a reference to the other.

A more complete understanding of the components, processes, assemblies, and devices disclosed herein can be obtained by reference to the accompanying drawings. These figures (also referred to herein as "FIG.") are merely schematic representations (e.g., illustrations) based on convenience and the ease of demonstrating the present disclosure, and are, therefore, not intended to indicate relative size and dimensions of the devices or components thereof and/or to define or limit the scope of the exemplary embodiments. Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

Turning now to FIG. 1, illustrating a simplified block diagram depicting the use of an automatic guidance system for guiding a brain probe to region of interest in the brain of a subject in need thereof. It is appreciated that the brain-probe can be, for example an electrode, such as a macro-electrode or a microelectrode. A plurality of electrode can be used simultaneously to record values of a plurality of insertion trajectories. As illustrated in FIG. 1 remote control 100 is provided, which can include trigger button 102 that can be configured to be pressed in order to automatically guide the electrode. The trigger button enables a driver initiation 104 and thus provides for electrode translation along a predetermined insertion trajectory. For example, so long as trigger button 102 is pressed by the user, the driver automatically moves the electrode through the various states (or locations) within the brain of a subject in need thereof, located along the predetermined insertion trajectory 106. The automatic movement (in other words, without human intervention of the distance or timing of insertion) of the electrode by the driver can be achieved due to closed loop feedback provided in the signal processing module, using for example, Partially Observable Markov Decision Process (POMDP).

Once the trigger button is released, the driver is stopped to provide time for the physician to verify accurate advancement of the electrode, and otherwise collect readings, thus utilizing the trigger button 102 as a safety mechanism.

Previously, electrode advancement was not automatic and thus included the following steps: the electrode was advanced by discrete steps, the physician pressed on a button, thus initiated a single step movement of the electrode, waiting period for verifying the position of the electrode, re-definition of step size and further pressing on the button to advance the electrode by another single step. Therefore, using the methods described herein, implemented using the systems provided, surgery time can be reduced by at least 50%, since the electrode is automatically advanced using closed loop feedback and advancement step-size can automatically be re-defined and implemented. The different locations within the STN can be identified in real time, while advancing the electrode, obviating the need for performing a full scan of the area beforehand.

Each time that an electrode is automatically advanced to a different site within the predetermined insertion trajectory, RMS and PSD are calculated 108 and the observed values for HMM output as DBN can be received by the signal processing module. The signal processing module can be configured to calculate the subsequent step size using the closed loop feedback. Typically an inverse proportion is exhibited between the resulting NRMS values and determined step size, meaning the higher is the NRMS value, the lower is the step size, since higher resolution is required closer to the electrode's installation in the region of interest.

The result of the closed loop feedback is demonstrated in blocks 110-116. In case the step size as determined is to be updated, as illustrated in block 110, the signal processing module, being in electronic communication with the driver coupled to the electrode automatically updates following step size, as illustrated in block 112. When step size does not have to be updated, as illustrated in block 114, plots, results and recommendations to the user are shown on a display as illustrated in block 116 and will be further described in detail (sere e.g., FIG. 3).

2A-2C, which are respectively a simplified pictorial illustration of the automatic guidance system for guiding a brain-probe to a region of interest (ROI) in the brain showing the brain-probe outside of the STN and including Table 1 (2A), a simplified pictorial illustration of the automatic guidance system for guiding a brain-probe to a region of interest (ROI) in the brain showing the brain-probe in the beginning of advancement within the STN and including Table 2 (2B) and a simplified pictorial illustration of the automatic guidance system for guiding a brain-probe to a region of interest (ROI) in the brain showing the brain-probe further advanced into the STN and including Table 3 (2C).

Figure 2A:
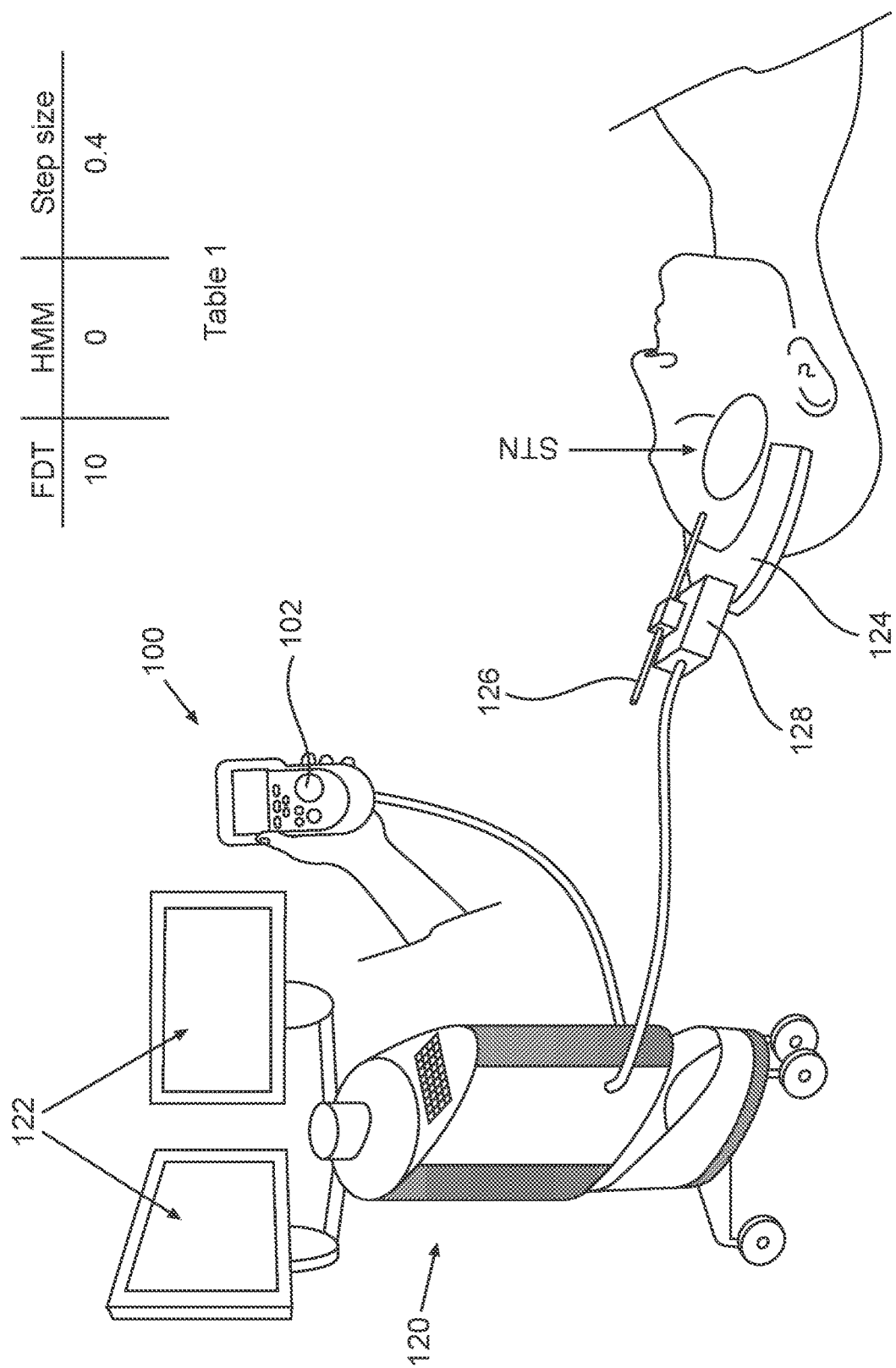
FIG. 2A, is a simplified pictorial illustration of an embodiment of the automatic brain-probe guidance system showing the probe outside of the STN and includes Table 1, while a simplified pictorial illustration of an embodiment of the automatic brain-probe guidance system showing the tool in the beginning of advancement within the STN including Table 2 is illustrated in FIG. 2B, and a simplified pictorial illustration of an embodiment of the automatic brain-probe guidance systems, showing the probe further advanced into the STN including Table 3 is illustrated in FIG. 2C.

As illustrated in FIG. 2A, the automatic guidance system for guiding a brain-probe to a target region in the brain can be utilized with NeuroOmega (AlphaOmega) or NeuroNav (Alphamega) system in the surgery room. The NeuroOmega or NeuroNav system is depicted by reference numeral 120, display 122 and remote control 100 are operably coupled thereto. An electrode 128 or plurality of electrodes 128 can be operably coupled to a frame 124, which can be configured to engage electrodes 126 relative to the skull of the patient and allow only longitudinal displacement of electrodes 126. Electrodes 126 can be operably coupled to driver 128, which automatically drives electrode 126 upon pressing of trigger button 102 on remote control 100.

Further, the tip of electrode 126 is illustrated as positioned outside of the STN in this first operative orientation. As seen in Table 1, the Estimate distance to target (EDT) at this first operative orientation of insertion trajectory is, for example 10 mm, with the HMM hidden or inferred state for the POMDM output being "0", indicating that electrode 126 is not positioned within any of the sub-territories of the STN and the step-size is determined to be 0.4 mm for example. It is appreciated that any EDT value and step-size can be utilized and are within the scope of the disclosure provided.

Figure 2B:
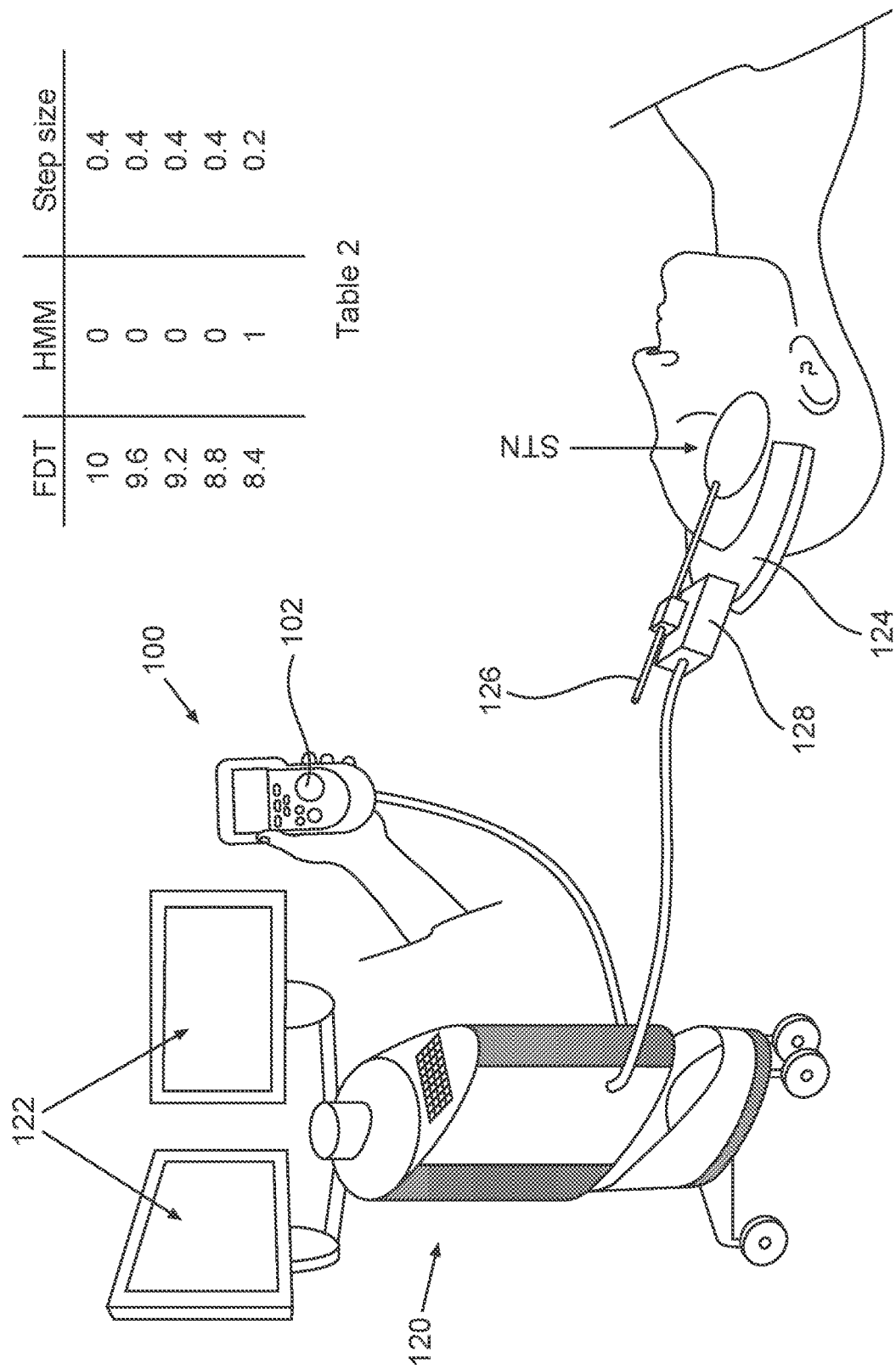

As seen in FIG. 2B, the automatic guidance system for guiding a brain-probe to a region of interest (ROI) in the brain is shown in a second orientation, where electrode 126 is positioned within the first region of the STN. As seen in Table 2, the Estimate distance to target (EDT) at this second operative orientation is 8.4 mm for example, with the HMM output being "1", indicating that the electrode 126 is positioned within the first sub-territory of the STN and the step-size can now be automatically reduced to, for example, 0.2 mm.

Figure 2C:
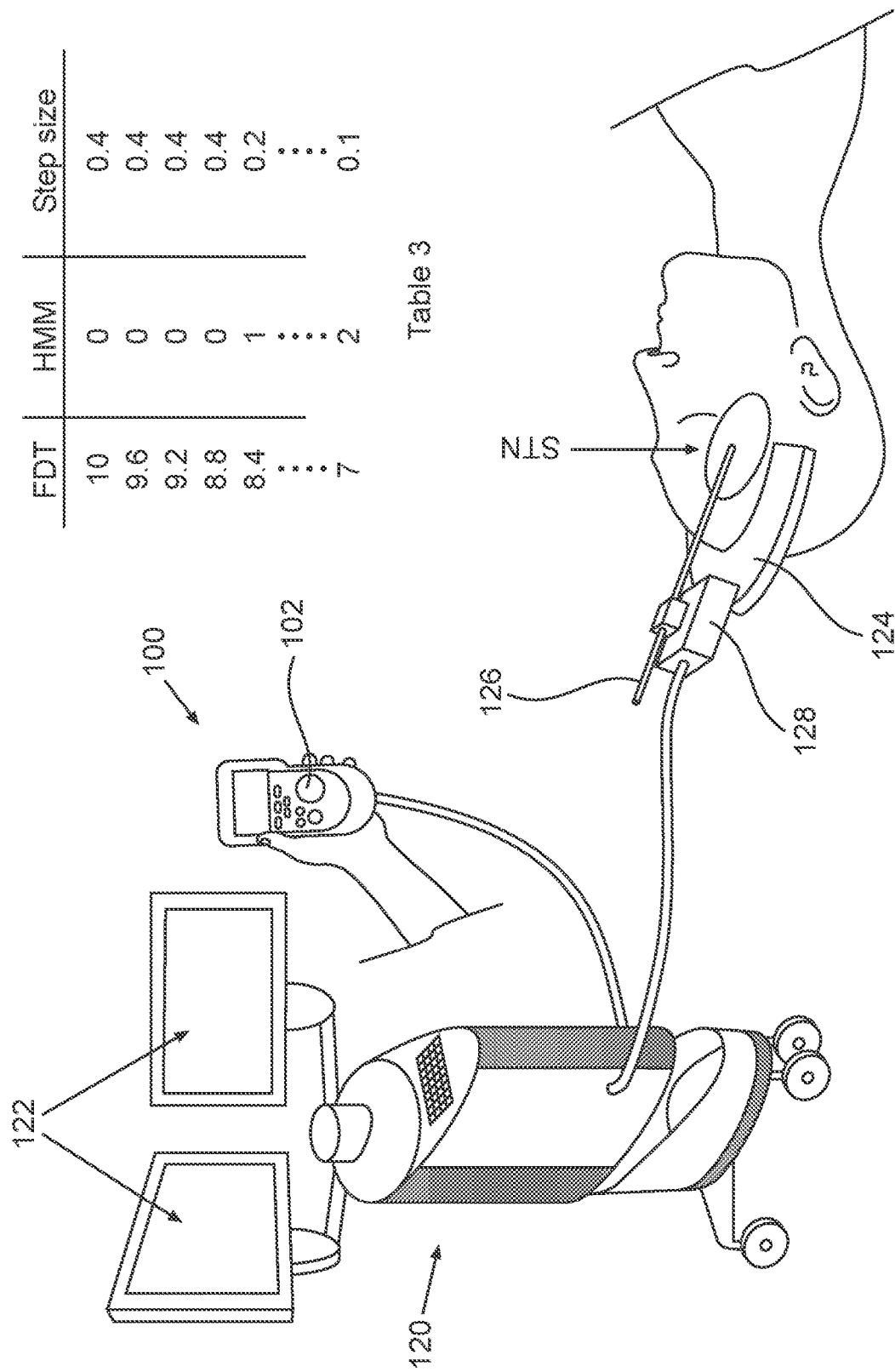

As illustrated in FIG. 2C, the automatic guidance system for guiding a brain-probe to a region of interest (ROI) in the brain is shown in a third operative orientation, where electrode 126 is positioned within the second region of the STN. As seen in Table 3, the Estimate distance to target (EDT) at this third operative orientation is, for example, 7 mm and the HMM hidden or inferred state output is "2", indicating that electrode 126 is positioned within the second sub-territory of the STN causing the step-size to now be automatically reduced to 0.1 mm for example. Electrode 126 can be displaced along the insertion trajectory passing regions of interest such as 1. the DLOR of the STN; 2. the region in the insertion trajectory before the STN; 3. the region inside the nonoscillatory STN; or 4. the region in the insertion trajectory after the STN. Or, in addition, 5—the region in the insertion trajectory within the substantia nigra (SNR). Electrodes 126 can be displaced through the above mentioned regions automatically following single pressing on trigger button 102 and the step size can also be automatically updated utilizing a closed loop feedback (e.g., factored Partially Observable Markov Decision Process (POMDP)).

Reference is made to FIG. 3, illustrating the graphic user interface shown on a display while using the automatic guidance system for guiding a brain-probe to a region of interest (ROI) in the brain. An exemplary user interface shown on display 122 as a result of displacement of a plurality of electrodes 126 through the insertion trajectory. As seen in FIG. 3, different regions in different EDT for each electrode can be depicted by different pattern. The user can then select the optimal location for macroelectrode implantation based on the results presented on display 122. For example, as illustrated in FIG. 3 electrode 1 entered region "1" at 6 mm EDT, region "2" at 0 mm EDT and region "3" at about −4 mm EDT (indicating the probe need to be retracted. Electrode 2 entered region "1" at 9 mm EDT, region "2" at 3 mm EDT and region "3" at about −1 mm EDT. Electrode 3 entered region "1" at 8 mm EDT, region "2" at 4 mm EDT and region "3" at about −3 mm EDT. The optimal trajectory can then be selected by the user and the macroelectrode can be implanted accordingly.

Detailed embodiments of the present technology are disclosed herein; however, it is to be understood that the disclosed embodiments are merely exemplary, which can be embodied in various forms. Therefore, specific structural and functional details disclosed herein are not to be interpreted as limiting but merely as a basis for the claims and as a representative basis for teaching one skilled in the art to variously employ the present technology in virtually any appropriately detailed structure. Further, the terms and phrases used herein are not intended to be limiting but rather to provide an understandable and enabling description.

The terms "first," "second," and the like, herein do not denote any order, quantity, or importance, but rather are used to denote one element from another. The terms "a", "an" and "the" herein do not denote a limitation of quantity, and are to be construed to cover both the singular and the plural, unless otherwise indicated herein or clearly contradicted by context. The suffix "(s)" as used herein is intended to include both the singular and the plural of the term that it modifies, thereby including one or more of that term (e.g., the probe(s) includes one or more probe). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

In addition, for the purposes of the present disclosure, directional or positional terms such as "top", "bottom", "upper," "lower," "side," "front," "frontal," "forward," "rear," "rearward," "back," "trailing," "above," "below," "left," "right," "horizontal," "vertical," "upward," "downward," "outer," "inner," "exterior," "interior," "intermediate," etc., are merely used for convenience in describing the various embodiments of the present disclosure.

One or more components may be referred to herein as "configured to," "configured by," "configurable to," "operable/operative to," "adapted/adaptable," "able to," "conformable/conformed to," etc. The terms (e.g. "configured to") can generally encompass active-state components and/or inactive-state components and/or standby-state components, unless context requires otherwise.

While in the foregoing specification the guidance systems for guiding a brain probe to a region of interest and their methods of facilitating have been described in relation to certain preferred embodiments, and many details are set forth for purpose of illustration, it will be apparent to those skilled in the art that the disclosure can be susceptible to additional embodiments and that certain of the details described in this specification and as are more fully delineated in the following claims can be varied considerably without departing from the basic principles of this invention.

What is claimed is:

1. A method of automatically guiding a driver coupled brain probe to a region of interest in the brain of a subject in need thereof, comprising:
    a. based on a predetermined insertion trajectory, positioning the brain probe toward the region of interest, the brain probe having a proximal end and a distal end coupled to a driver;
    b. using a predetermined step size, translating the brain probe toward the region of interest;
    c. recording a neurophysiological response by the brain probe along the predetermined insertion trajectory;
    d. based on the recorded neurophysiological response by the brain probe, calculating a plurality of predetermined observation elements;
    e. constructing a Bayesian Network for each observation element;
    f. combining the Bayesian Network constructed for each observation element thereby creating a Dynamic Bayesian Network including the plurality of the predetermined observation elements;
    g. based on the Dynamic Bayesian Network, constructing a Factored Partially Observable Markov Decision Process, wherein the Partially Observable Markov Decision Process (POMDP) further comprises relations between the predetermined observation elements;
    h. based on the POMDP, determining a distance step to advance the brain probe along the insertion trajectory;
    i. using the driver, automatically advancing the brain probe toward the region of interest along the insertion trajectory; and
    j. repeating the step of determining the distance step and advancing the brain probe to the location of interest.

2. The method of claim 1, wherein the region of interest is a sub-territory of the subthalamic nucleus (STN).

3. The method of claim 2, wherein the sub-territory of the STN is the dorsolateral oscillatory region (DLOR) of the STN.

4. The method of claim 1, wherein the step of positioning the brain probe toward the region of interest is preceded by providing reference values for each of the plurality of observation elements for a statistically-significant number of locations along the insertion trajectories.

5. The method of claim 4, wherein the locations for which the reference values for each of the plurality of observation elements is provided are: the DLOR of the STN and/or the region of the insertion trajectory immediately before the STN and/or the region inside the nonoscillatory STN and/or the region of the STN immediately following the STN.

6. The method of claim 5, further comprising the step of providing reference values for each of the plurality of observation elements for the region inside the substantia nigra (SNR).

7. The method of claim 4, further comprising assigning to each location along the insertion trajectory a probability value.

8. The method of claim 1, wherein the brain probe is an electrode.

9. The method of claim 8, comprising providing deep brain stimulation.

10. The method of claim 9, further comprising:
    a. Removing the electrode; and
    b. Inserting a macroelectrode into the region of interest.

11. The method of claim 10, wherein the region of interest is the DLOR of the STN.

12. The method of claim 9, wherein the neurodegenerative disease and/or disorder is a brain injury, a neurodegenerative disorder, stroke, epilepsy, or Parkinson's disease.

13. The method of claim 1, wherein said recording comprises recording a neurophysiological response by recording discharges by the brain probe along the predetermined insertion trajectory.

14. The method of claim 13, wherein the neurophysiological response recorded by the brain probe is neuronal firing rate, local field potential or a combination of neurophysiological responses comprising one or more of the foregoing.

15. The method of claim 13, further comprising analyzing the neurophysiological response within the beta frequency band range to determine a value of beta oscillatory activity.

16. The method of claim 15, wherein the plurality of observation element based on the recorded neurophysiological response comprise a mean beta power spectral density (PSD) and/or maximum beta PSD and/or root mean square (RMS) of the beta oscillatory activity values.

17. The method of claim 13, wherein the plurality of observation elements based on the recorded neurophysiological response comprises normalized RMS (NRMS).

18. An automatic brain-probe guidance system comprising:
   a. a brain probe having a proximal end and a distal end, the proximal end configured to record a neurophysiological response along an insertion trajectory of said brain probe, and the distal end operably coupled to a driver;
   b. the driver, operably coupled to the brain probe;
   c. a processing module in communication with the brain probe and the driver, comprising:
   (A) a neurophysiological response processor in communication with the brain probe, comprising a memory having a processor-readable medium thereon with a set of executable instructions thereon configured to (i) record a plurality of neurophysiological responses by the brain probe; and (ii) based on the recorded neurophysiological responses by the brain probe, calculate at least one predetermined observation element; and
   (B) a step determining processor, in communication with the driver and neurophysiological response processor, the step determining processor comprising a memory having a processor-readable medium thereon with a set of executable instructions configured to (i) automatically determine a distance step to advance the brain probe along said insertion trajectory based on the calculated at least one predetermined observation element;
   d. a controller operably coupled to the driver wherein said controller operates said driver to move said probe according to said determined distance step; and
   e. a display, in communication with the processing module.

19. The system of claim 18, wherein the set of executable instructions of said memory of said step determining processor is configured to:
   i. construct a Bayesian Network for each of the at least one observation element;
   ii. combine a plurality of Bayesian Networks constructed for each observation element thereby creating a Dynamic Bayesian Network including the at least one predetermined observation element;
   iii. based on the Dynamic Bayesian Network, construct a Factored Partially Observable Markov Decision Process, wherein the factored Partially Observable Markov Decision Process (POMDP) further comprises relations between the predetermined observation elements;
   iv. based on the POMDP, determine said distance step to advance the brain probe along the insertion trajectory.

20. The system of claim 19, wherein the neurophysiological response recorded by the brain probe is neuronal firing rate, local field potential or a combination of neurophysiological responses comprising one or more of the foregoing.

21. The system of claim 20, wherein the set of executable instructions in the neurophysiological response processor is further configured to: analyze the neurophysiological response within the beta frequency band range to determine a value of beta oscillatory activity, wherein the at least one predetermined observation element based on the recorded neurophysiological response is a mean beta power spectral density (PSD) and/or maximum beta PSD and/or root mean square (RMS) and/or normalized RMS of the beta oscillatory activity values.

22. The system of claim 21, wherein the set of executable instructions in the step determining processor is further configured to assign to each of a plurality of locations along the insertion trajectory a probability value, wherein the locations are the DLOR of the STN and/or the region of the insertion trajectory immediately before the STN and/or the region inside the nonoscillatory STN and/or the region of the STN immediately following the STN.

23. The system of claim 22, wherein the memory in the step determining processor further has reference values for each of the at least one predetermined observation elements for the region inside the substantia nigra (SNR) stored thereon.

24. The system of claim 19, wherein the memory in the step determining processor further has reference values for each of the at least one predetermined observation elements for the locations along the insertion trajectory stored thereon.

25. The system of claim 19, wherein the set of executable instructions in the memory of the neurophysiological response processor is further configured to: analyze the neurophysiological response wherein the at least one predetermined observation element based on the recorded neurophysiological response is a normalized RMS (NRMS).

26. The system of claim 18, wherein the brain probe is an electrode and wherein the system further comprises a macroelectrode, configured to provide deep brain stimulation.

27. The system of claim 18, wherein the brain probe is configured to provide deep brain stimulation.

28. The system of claim 18, wherein said signal processing module is configured to update a predetermined step size based on the calculated at least one predetermined observation element.

29. The system of claim 18, wherein said set of executable instructions of said step determining processor is configured to (i) assign a probability value to each of a plurality of locations or states along said insertion trajectory, wherein each of said probability values illustrates a probability of said calculated at least one predetermined observation element to be associated with a selected location or state along said insertion trajectory and (ii) said automatically determine said distance step to advance the brain probe along said insertion trajectory based on said probability values.

30. The system of claim 18, wherein said calculated at least one predetrmined observation element comprise measurements of power spectral density (PSD) and/or root mean square (RMS) of beta oscillatory activity values.

* * * * *